United States Patent
Bannister et al.

(10) Patent No.: US 9,839,553 B2
(45) Date of Patent: Dec. 12, 2017

(54) AUTOMATED ORTHOTIC DEVICE WITH TREATMENT REGIMEN AND METHOD FOR USING THE SAME

(71) Applicant: Bio Cybernetics International, Inc., La Verne, CA (US)

(72) Inventors: Ed Bannister, Riverside, CA (US); Michael L. Martin, Bainbridge Island, WA (US); Sai Chung Chan, Irvine, CA (US); Matthew V. Waidelich, La Verne, CA (US); Dipankar Ghosh, Irvine, CA (US); Roberto A. Lucero, Anaheim, CA (US); Oscar A. Villa, Newport Beach, CA (US); John W. Berger, Laguna Niguel, CA (US); Jeffery W. Barnhouse, San Dimas, CA (US)

(73) Assignee: BIO CYBERNETICS INTERNATIONAL, INC., La Verne, CA (US)

( * ) Notice: Subject to any disclaimer, the term of this patent is extended or adjusted under 35 U.S.C. 154(b) by 456 days.

(21) Appl. No.: 13/829,991

(22) Filed: Mar. 14, 2013

(65) Prior Publication Data

US 2013/0345612 A1 Dec. 26, 2013

Related U.S. Application Data

(60) Provisional application No. 61/662,198, filed on Jun. 20, 2012.

(51) Int. Cl.
*A61F 5/00* (2006.01)
*A61F 5/02* (2006.01)
(Continued)

(52) U.S. Cl.
CPC ............... *A61F 5/02* (2013.01); *A61B 5/0004* (2013.01); *A61B 5/1116* (2013.01);
(Continued)

(58) Field of Classification Search
CPC .... A61F 5/02; A61F 5/028; A61F 2005/0188; A61H 2011/005; A61H 2230/625; G06F 19/3481
(Continued)

(56) References Cited

U.S. PATENT DOCUMENTS 5,346,461 A * 9/1994 Heinz ................. A61F 5/028
128/121.1
6,872,187 B1 * 3/2005 Stark ................. G06F 19/3418
482/8

(Continued)

FOREIGN PATENT DOCUMENTS

WO 02060311 A2 8/2002

OTHER PUBLICATIONS

PCT Communication Relating to the Results of the Partial International Search for International Application No. PCT/US2013/044901, dated Sep. 17, 2013 (3 pp.).
(Continued)

*Primary Examiner* — Kim M Lewis
(74) *Attorney, Agent, or Firm* — Holland & Hart

(57) ABSTRACT

An automated orthotic device with a treatment regimen and a method for using an automated orthotic device with a treatment regimen to provide a plurality of prescribed tension settings. The orthotic device may comprise a body brace, a controller, a data storage means, and a communication means to address the problem of patients being required to visit the physician's office every time an adjustment must be made in the prescribed tension setting in their automated orthotic device. In one embodiment, a plurality of
(Continued)

prescribed tension settings in the automated orthotic device are sorted so that as the patient's condition improves, the next prescribed tension setting in the treatment regimen may be applied. In another embodiment, the physician is allowed to edit or supplement a patient's treatment regimen remotely by connecting to the automated orthotic device over a network.

21 Claims, 12 Drawing Sheets

(51) Int. Cl.
    *A61B 5/11*     (2006.01)
    *A61B 5/00*     (2006.01)
    *G06F 19/00*     (2011.01)
    *A61F 5/01*     (2006.01)
    *A61H 11/00*     (2006.01)

(52) U.S. Cl.
    CPC ............ *A61B 5/4833* (2013.01); *A61F 5/028* (2013.01); *A61F 2005/0188* (2013.01); *A61H 2011/005* (2013.01); *A61H 2201/501* (2013.01); *A61H 2230/625* (2013.01); *G06F 19/3481* (2013.01)

(58) Field of Classification Search
    USPC ....... 602/19, 5; 606/204; 601/134, 142–144, 601/149, 152; 128/96.1, 97.1, 98.1, 99.1, 128/100.1, 101.1
    See application file for complete search history.

(56) References Cited

U.S. PATENT DOCUMENTS

| | | |
|---|---|---|
| 2002/0013516 A1 | 1/2002 | Freyre et al. |
| 2003/0130692 A1 | 7/2003 | Porrata et al. |
| 2005/0043660 A1 | 2/2005 | Stark et al. |
| 2005/0245853 A1 | 11/2005 | Scorvo |
| 2007/0155588 A1 | 7/2007 | Stark et al. |
| 2010/0331750 A1 | 12/2010 | Ingimundarson |
| 2011/0015708 A1 | 1/2011 | Lee et al. |
| 2011/0230806 A1* | 9/2011 | Lou et al. ..................... 602/13 |
| 2012/0078145 A1 | 3/2012 | Malhi et al. |

OTHER PUBLICATIONS

PCT International Search Report for International Application No. PCT/US2013/044901, dated Jan. 8, 2014 (7 pp.).

\* cited by examiner

Automated Orthotic Device With Treatment Regimen System 80

Physician PC Automated Orthotic Device Interface System 120

AUTOMATED ORTHOTIC DEVICE WITH TREATMENT REGIMEN AND METHOD FOR USING THE SAME

CROSS-REFERENCE TO RELATED APPLICATIONS

This application claims priority from U.S. Provisional Patent Application No. 61/662,198, filed on 20 Jun. 2012, the contents of which are incorporated herein by reference in their entirety.

BACKGROUND OF THE INVENTION

The present invention relates generally to automated orthotic devices, and methods for using an automated orthotic device, and more particularly to an automated body brace for medical or recuperative purposes having the ability to implement a treatment regimen.

An orthotic device or orthosis (commonly known as a brace or splint) is an orthopedic device that is typically applied to a limb or the body. Among other things, the purpose of such a device can be to provide support, protection, pain reduction, or replacement of lost function.

In this regard, a common method of alleviating pain in people suffering from back pain or injuries and promoting healing in post-operative back surgery patients is to stabilize the spine using an orthosis, such as a brace. There are a large variety of braces available depending on the diagnosis and physical needs of the individual. These devices include a multitude of construction materials and designs which can be snugly fitted around the patient's trunk and peripheral area, such as the cervical and pelvic regions.

Such braces are effective in achieving spinal stability if worn properly and consistently, but many patients have difficulty manually adjusting the brace to a tight enough fit for providing adequate support. This is especially true for post-operative patients who are in pain and lack sufficient strength. Patient non-compliance reduces the effectiveness of the brace.

Another drawback of existing braces is their inability to adapt as the patient moves from a standing position to a sitting position. A sitting position may require a different brace tension than a standing position. Further, it is difficult to adjust the brace to have exactly the same amount of tension or even to set a particular tension for a particular patient.

In an attempt to solve some of these issues, prior art back braces include automated back braces that can automatically set the brace to a specified compression or tension level. However, as the patient's condition changes, it might desirable to change the prescribed tension setting. To make such a change, the patient must return to the physician's office. This can be inconvenient for the patient.

Existing automated braces can change their tension settings for sitting and standing positions, but the user must manually activate the change such as by pushing a button on a control module. This can be cumbersome and embarrassing in social situations.

It can readily be appreciated that there is a need for an automated brace that can adjust as a patient's condition changes without the patient being required to return to the doctor's office. It can further be appreciated that there is a need for an automated brace that can adjust the support according to the user's position, without the need for the user to manually adjust the settings. The present invention fulfills these needs and provides further related advantages.

SUMMARY OF THE INVENTION

The present invention is embodied in an automated orthotic device comprising a brace and a controller that provides a specified level of support to certain parts of the human body. In one embodiment, the subject invention addresses the problem of a patient having to visit the physician's office every time the prescribed tension setting must be changed, by allowing the physician to store an entire treatment regimen in the brace so that the brace will move to the next prescribed tension setting in the treatment regimen after the passage of a certain amount of time or at the user's command.

In one embodiment, the automated orthotic device comprises a body brace configured to be worn around a portion of a human body, a data storage means, and a controller. The data storage means is configured to store a treatment regimen program that has been determined by a physician and the treatment regimen program comprises a plurality of prescribed tension settings to be carried out in a specified order. The controller is configured to carry out the treatment regimen program by causing the body brace to apply each of the prescribed tension settings according to the specified order of the treatment regimen program.

In another embodiment, the treatment regimen program further comprises a set period of time associated with each of the plurality of prescribed tension settings. The controller is further configured to carry out the treatment regimen program by causing the body brace to apply each of the prescribed tension settings according to the specified order and for the specified period of time for each tension setting specified by the treatment regimen program.

In another embodiment, the controller is configured to apply each of the prescribed tension settings until the user inputs a command to move to the next prescribed tension setting in the treatment regimen program.

In one embodiment, the body brace and controller are further configured to detect brace usage data and the data storage means is further configured to store this brace usage data. The brace usage data may include data on the length of time a user has worn the automated orthotic device and data on the tension settings applied while being worn.

In another embodiment, the treatment regimen program further comprises a set period of time associated with each of the plurality of prescribed tension settings wherein the set period of time specifies the period of time that the automated orthotic device must be worn by the user at the associated prescribed tension setting. The controller is configured to carry out the treatment regimen program by detecting and storing the amount of time the user has worn the automated orthotic device at the current prescribed tension setting and then moving to the next prescribed tension setting in the treatment regimen when the user has worn the automated orthotic device at the prescribed tension setting for the specified amount of time associated with that prescribed tension setting.

In another embodiment of the present invention, the automated orthotic device also includes a network connection means, which allows the controller to receive data from a network and transmit data to a network. Through this network connection means, the automated orthotic device is able to receive a treatment regimen program or receive changes to the current treatment regimen program from a remote computer on the network.

In another embodiment of the present invention, the automated orthotic device also includes a user position detection means. The user position detection means is configured to automatically detect changes in position by a user and adjust the tension setting in response to the user's change in position.

In one embodiment, the user position detection means may be an accelerometer.

The present invention is also embodied in a method for using an automated orthotic device with a treatment regimen. The automated orthotic device comprises a body brace configured to be worn around a portion of a user's body, a data storage means, and a controller. The treatment regimen program comprises a plurality of prescribed tension settings to be carried out in a specified order. The method comprises the steps of receiving a treatment regimen program in an automated orthotic device, storing the treatment regiment program on the data storage means, and applying each of the plurality of tension settings according to the specified order in the treatment regimen program.

The present invention is also embodied in a method for using an automated orthotic device with a treatment network. The method comprises the steps of connecting the automated orthotic device to a network, receiving a prescribed tension setting from a remote computer on the network, storing the prescribed tension setting on a data storage means, and applying the prescribed tension setting around a portion of the user's body.

The present invention is also embodied in a method for using an automated orthotic device with a user position detection means. The method comprises the steps of applying a first prescribed tension around a portion of a user's body, detecting a change in position by the user, and then applying a second prescribed tension setting around the portion of the user's body in response to the detected change in position.

These and other features and advantages of the invention should become more readily apparent from the detailed description of the preferred embodiments set forth below taken in conjunction with the accompanying drawings, which illustrate, by way of example, the principles of the invention.

BRIEF DESCRIPTION OF THE DRAWINGS

Embodiments of the present invention will now be described, by way of example only, with reference to the following drawings.

DETAILED DESCRIPTION OF THE PREFERRED EMBODIMENTS

Figure 1:
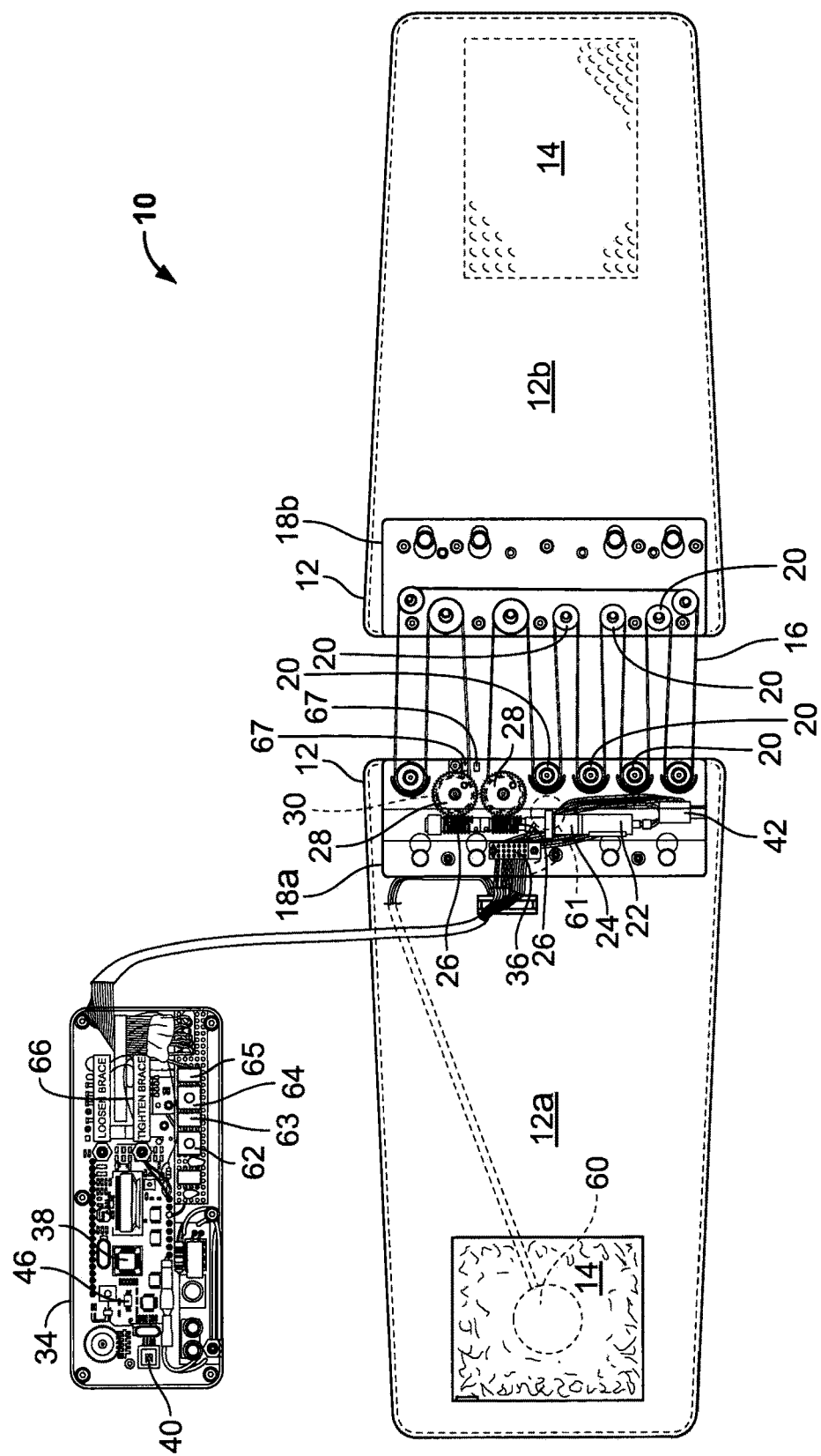
FIG. 1 is a planar view of an automated orthotic device in accordance with an embodiment of the present invention.

With reference to FIG. 1, there is shown an automated orthotic device 10 in accordance with an embodiment of the present invention. The automated orthotic device 10 comprises a body brace 12. The body brace 12 is adapted to be wrapped around the trunk of a patient. The body brace 12 comprises two brace segments, 12a and 12b, each carrying part of a means for automatically tightening the brace. A section of hook-and-loop fastener fabric 14 is mounted on opposite sides of each brace segment at the free opposite ends thereof for securing the two free ends together after the brace is wrapped around the patient's trunk. Such material can withstand a large amount of shear stress so that the brace 10 may be kept under tension but can be easily peeled away when the apparatus is to be taken off.

The means for automatically tightening the brace can include a cable 16 and a plate 18a or 18b mounted on each brace segment. Each plate 18a or 18b has a series of pulleys 20 mounted on it at staggered positions relative to the other plate. Center points (e.g., point 32) of the pulleys are also distributed across one or more plate. The cable 16 runs serially through the pulleys 20 and is fixed at each end in a manner described more fully below so as to hold the brace segments in position. Pressure sensors 60, 61 are placed in the belt to check the tightness of the belt. One pressure sensor 60 is placed on the abdomen, and the other pressure sensor 61 is placed on the back.

Figure 2:
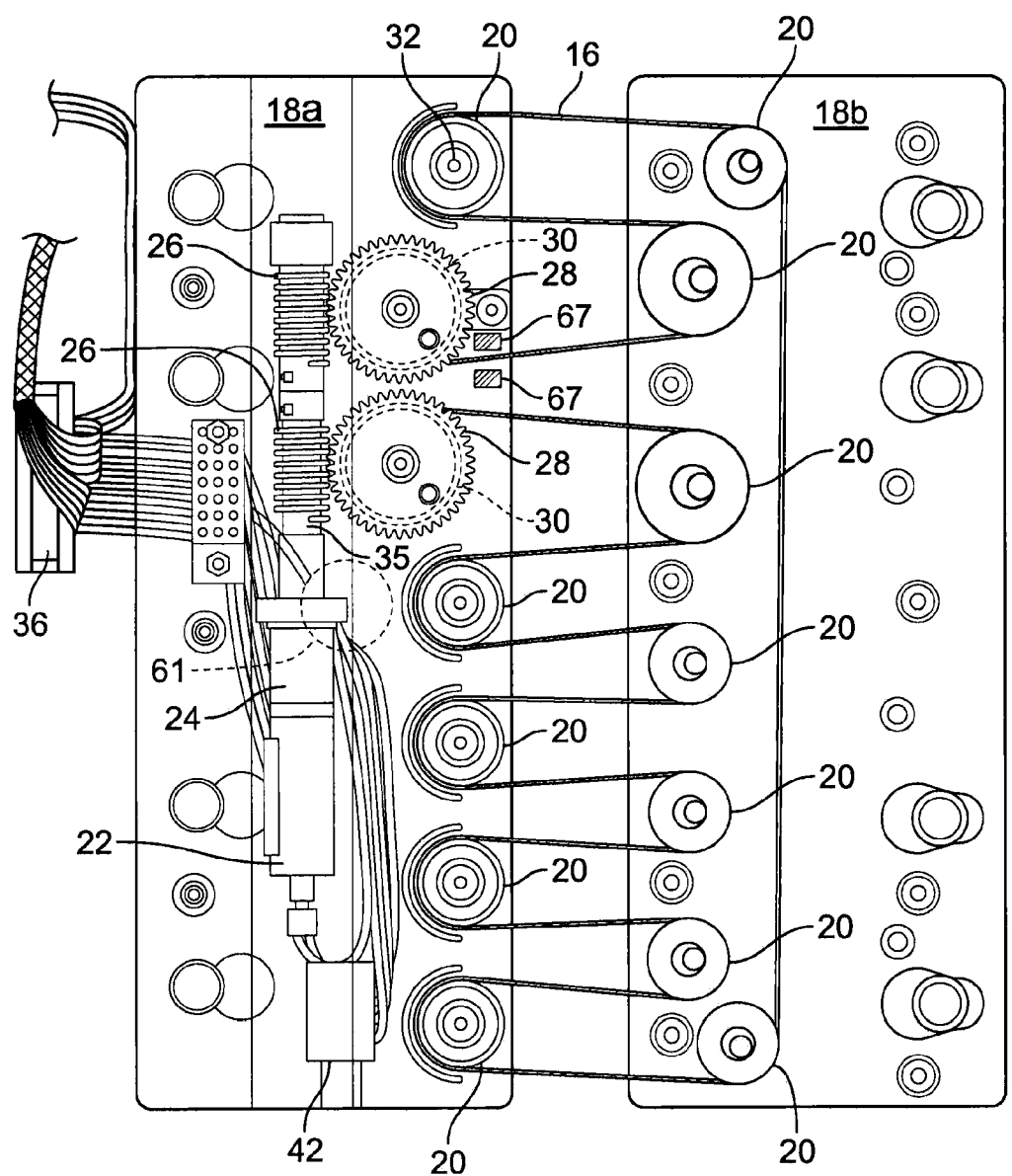
FIG. 2 is a close-up view of an automated tightening mechanism that is part of the automated orthotic device of FIG. 1.

FIG. 2 shows part of the means for automatically tightening the brace, including the pair of plates 18a and 18b in greater detail. An electric motor 22, a motor shaft 24, worms 26, and worm gears 28 are mounted on one of the plates 18a or 18b and are mechanically coupled together so that rotation of the motor 22 causes rotation of worm gears 28. A spool 30 is coaxially attached to each worm gear 28, and the two ends of cable 16 are attached to each of the spools 30. The motor 22 thus reels the cable 16 in or out to determine the cable's operative length. Optical sensors 67 may be used to determine the home and end positions of motor travel. The cable 16 runs through the pulleys 20 on each brace segment in alternating fashion so that shortening of the operative length of the cable by the motor 22 pulls the two brace segments 12a and 12b closer together and tightens the body brace 12 around the patient's trunk with a mechanical advantage.

Figure 12:
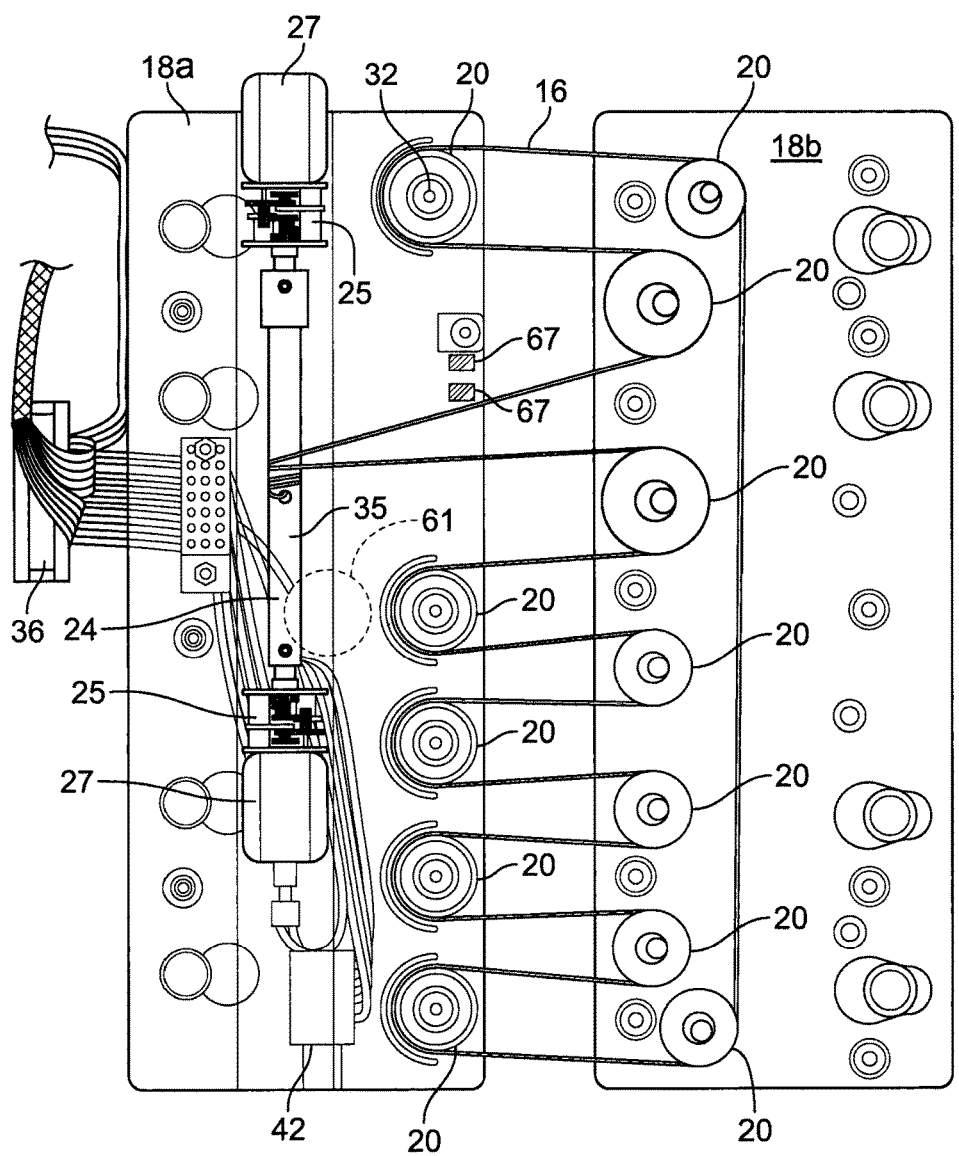
FIG. 12 is a close-up view of a wormless automated tightening mechanism that may be incorporated in the automated orthotic device of FIG. 1.

In one embodiment, shown in FIG. 12, the worm gears 26 and 28 may be omitted by connecting the string 16 directly to the motor shaft 24. Additionally, the single electric motor 22 of FIG. 2 may be replaced by dual motors 27 connected to opposite ends of shaft 24. This embodiment allows for removal of worm gears 26 and 28, thereby reducing the cost of manufacture and improving overall system efficiency. Causing the two motors 27 to turn in opposite directions causes both motors 27 to turn the shaft 24 in the same direction. The two motors 27 turn the shaft 24 to either reel the cable 16 in or out to determine the cable's operative length. The motors 27 make use of reduction gears 25. Motors having larger reduction gear ratios yield smaller decreases in drive force when power is removed from the motor. As such, each of the dual motors would preferably have a sufficiently large reduction gear ratio for the motors to maintain the force of the brace around a user even when power is not supplied to the motors. A force of 70 Newtons is the amount of drive force believed to be sufficient to target ~95.6% of the population.

Figure 3:
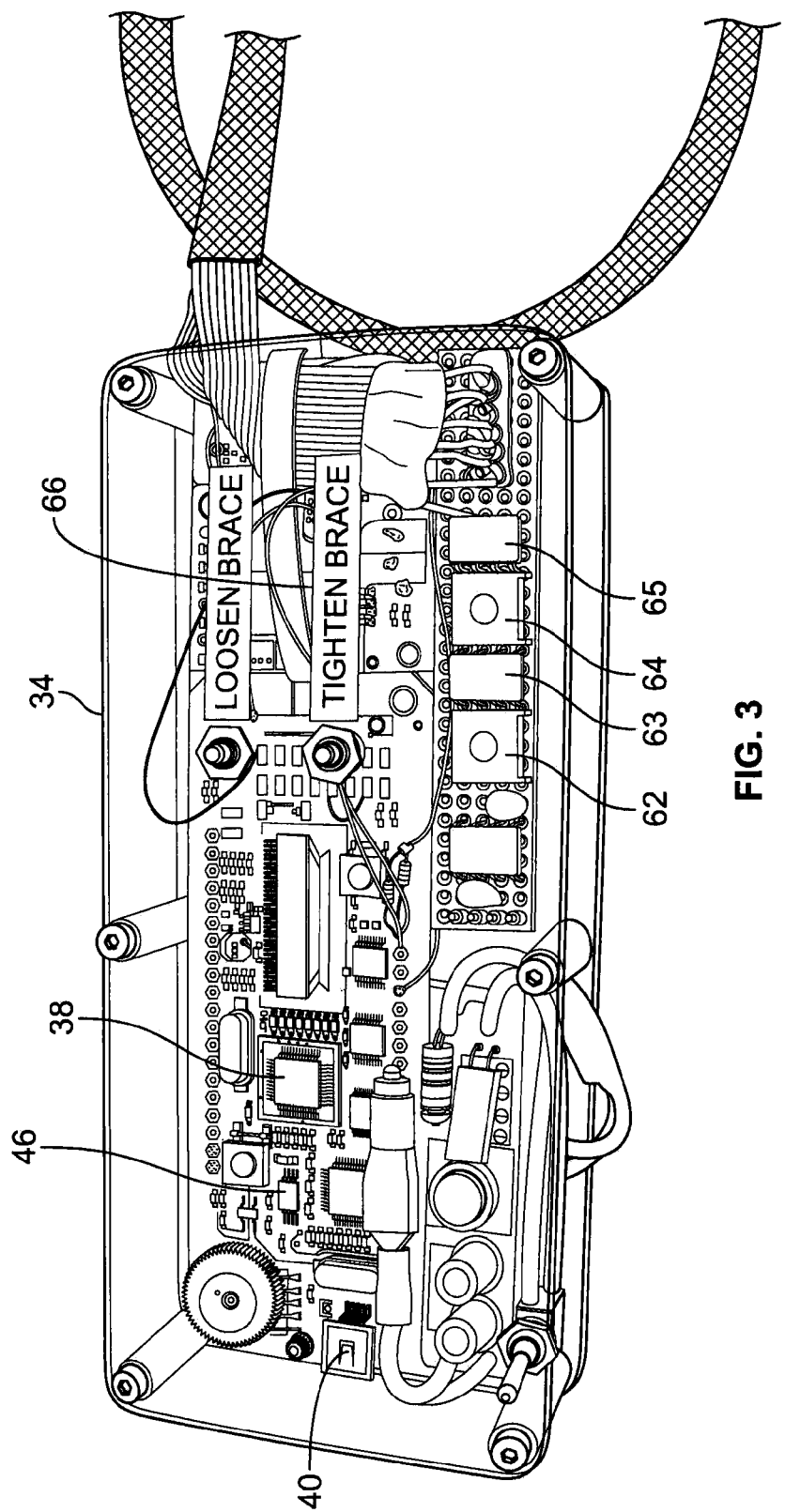
FIG. 3 is a close-up view of controller for the automated orthotic device of FIG. 1.

FIG. 3 shows in greater detail the controller 34 for controlling the means for automatically tightening the brace. The controller 34 can include a control module 36 mounted on one of the plates 18*a* or 18*b*. The controller comprises a microprocessor 38. The controller also includes a motor controller 66. The motor controller 66 in FIG. 3 shows a self-contained single-chip motor controller. This device, under directions from the microprocessor 38, is able to provide both direction control and speed control for tightening or loosening the brace 10. In one embodiment during the tightening process, pressure sensors 60, 61 are used to measure the pressure of the belt to determine the correct tightness. The pressure sensor reading can constitute a setting for the brace and may be stored for later recall on a storage device 46. In FIG. 3, microprocessor 38 has 64 KB of built-in flash memory for storage device 46. Trim pots 62, 64 and op amps 63, 65 are used to amplify the pressure sensor input for analog to digital conversion (ADC). The ADC values are sent to the microprocessor for determination of the correct tightness or looseness of the brace.

In another embodiment, the microprocessor counts the number of rotations made by the motor by optically coupling the motor to the microprocessor's data input circuitry. That number of motor rotations can constitute a setting for the brace and be stored for later recall on the storage device 64. If the number of turns of the motor shaft is used as the setting for the tension of the brace, the tension is repeatable for the same patient. However, because a certain number of turns of the motor shaft 35 is not equivalent to magnitude of tension, i.e., smaller patients may require more turns of the shaft to achieve the same tension as larger patients, the tension of the brace is not presentable to a certain degree of tension.

In another embodiment, the microprocessor 38 monitors and stores the output of a strain gauge either connected within the material of the brace or connected to the cable. The strain gauge measures the tension of the brace. The strain gauge can be a spring-loaded linear potentiometer attached at either end of the cable.

In one embodiment, the controller 34 uses monitoring of the motor current as an indirect indicator to measure the tension in the back brace. If the motor 22 is driven by a MOSFET H-bridge, one of the MOSFETs used to drive the motor can be used in conjunction with the resistor below it to obtain an indication of the tension. An A/D converter can be used to measure the voltage drop across the resistor to indicate the motor current and thus the relative tension on the cable, which is proportional to the tension of the brace. The motor current is periodically polled by the microprocessor.

Additionally, the microprocessor 38 can be adapted to continuously or periodically sense the tension of the brace. Periodic sensing can be accomplished by momentarily turning the motor 22 on. The motor 22 is turned on only to check the tension vis-à-vis its current consumption. This can be accomplished very quickly without tightening or loosening the brace. Since the microprocessor 38 has available the information of the last set tension, by periodically checking the motor current consumption/brace tension and comparing it with what it should be in accordance with the last set tension, it is possible for the microprocessor 38 to determine whether the brace has been taken off. That is, if a patient takes the brace 10 off in the fully tightened condition (which is possible since the brace is held in the front by hook-and-loop fasteners 14), and no loosening of the cable occurs, it will be difficult for the patient to put the brace back on. The microprocessor 38 would sense that the brace is off of the patient, and that there is no tension on the cable 16. When the microprocessor 38 senses that the brace 10 has been taken off, it can unspool the cable 16 so that the brace 10 is automatically ready to be put back on. In one embodiment the microprocessor 38 is configured to poll the current setting and compare it to the last setting every 15 seconds. The timing of the polling can be set to other values.

Continuous sensing of the tension level is most desired, and with continuous or at least short-interval periodic sensing, continuous or semi-continuous adjusting of the tension can be obtained. Continuous sensing may be achieved by, instead of periodically turning the motor 22 on to check the tension of the brace, leaving the microprocessor 38 on continuously to check and adjust the tension of the brace 10. In this manner, precise automatic control of the brace can be obtained. The patient can then have the same level of comfort and compliance with the tension required without any additional input. In one embodiment, a mechanical gear lock is used to maintain tension, thus relieving the need to use the motor 22 to maintain tension. Thus, battery consumption can be reduced and motor life can be extended.

The controller 34 also comprises a storage device 46, possibly a magnetic or optical disk or a solid state drive. The storage device 46 can be used to store prescription data, including a treatment regimen. Prescription data is downloaded onto the controller 34 through an interface device 40. The interface device 40 allows the controller to be connected to a computer or a network. It will be understood that connecting to a network may involve connecting to a computer that is on the network, and connecting to a computer may involve connecting to a network that includes the computer. This connection may be achieved through standard computer connections such as USB or Bluetooth, or through standard network connections such as a WiFi or Ethernet. The network can be the Internet or some local area or wide area network. In one embodiment, means are provided to safeguard prescription data through an encryption scheme or other protection mechanism.

The patient's physician connects his or her computer to the automated orthotic device 10 through the interface device 40. This connection may be accomplished directly between the physician's computer and the orthotic device 10, or it may be a connection over a network. Once the physician's computer and the orthotic device 10 are connected, the physician's computer can upload a treatment regimen to the automated orthotic device 10. In one embodiment. this treatment regimen can be a single prescribed tension setting. In another embodiment, the treatment regimen can be multiple tension settings to be applied as the patient's condition changes or over certain prescribed time intervals. The automated orthotic device 10 may apply the next prescribed tension setting in the treatment regimen after a certain time period, with the orthotic device 10 automatically changing the prescribed setting after a set amount of time or after a set number of hours of use, or the changes can be implemented by user command through controller 34, with the user determining when he or she feels that his or her condition is improving enough to adjust the tension setting to the next prescribed setting. By storing an entire treatment regimen on the storage device 46, the patient can avoid multiple trips to the physician's office to receive adjustments to the prescribed tension setting.

When changes must be made to the treatment regimen, the current invention allows for these changes to be made without the patient going into the physician's office. The interface device 40 allows for the patient to connect the orthotic device to the physician's computer over a wide area network. Through this connection, the physician may upload a new prescribed tension setting or a revised treatment regimen to the controller 34, which would then be stored in the storage device 46. The controller 34 could include an override to allow the user to adjust the tension in the brace to a non-prescribed tension if the tension prescribed by the physician causes discomfort, which may be caused by swelling or changes in the patient's condition.

In addition to storing prescription settings or a treatment regimen, the storage device 46 can also be used to store usage data. Continuous or periodic sensing allows the controller 34 to monitor how many hours a day the back brace is being used, at what tension, and whether the user has changed the tension away from the prescribed tension setting. This information can be sent to the physician so that the physician can monitor the patient's compliance with the prescribed treatment. This information can include a complete hour-by-hour history of the use of the brace, along with the associated tension.

The orthotic device 10 also includes a posture detection device 42 to automatically determine whether the patient is standing or sitting. In one embodiment, the posture detection device 42 is an accelerometer. The posture detection device 42 may communicate with the microprocessor 38 in the controller 34 to automatically set the orthotic device 10 to different tension settings when the patient is sitting and when the patient is standing.

Figure 4A:
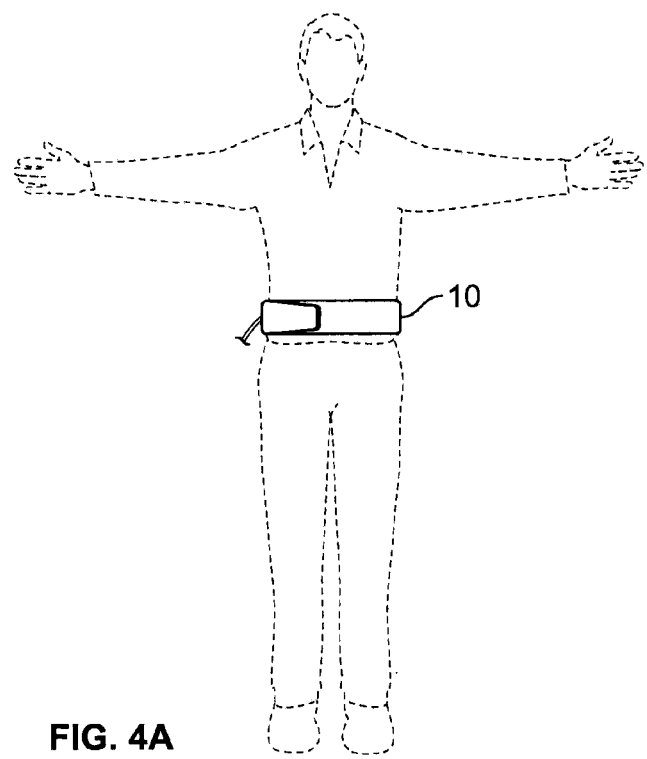
FIG. 4A is a perspective view of the orthotic device of FIG. 1 being worn by a person while standing.
Figure 4B:
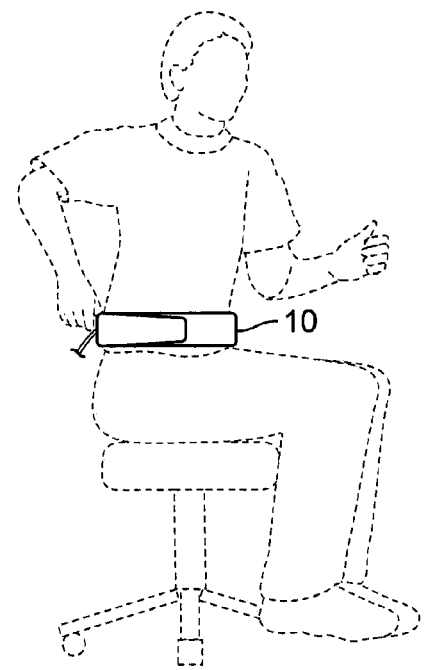
FIG. 4B is a perspective view of the orthotic device of FIG. 1 being worn by a person while sitting.

With reference to FIGS. 4A and 4B, there is shown a patient using the orthotic device 10 while standing and while sitting, respectively. As an example of how this automatic tension adjustment would work, if the posture detection device 42 is an accelerometer, when the patient puts the orthotic device 10 on, the orthotic device automatically applies the prescribed standing tension specified by the patient's physician. When the patient sits down, the accelerometer measures the acceleration and sends this acceleration data to the microprocessor 38. The microprocessor 38 analyzes the acceleration data and determines that the patient is now sitting and causes the orthotic device 10 to apply the prescribed sitting tension specified by the patient's physician. In another embodiment, rather than having the patient's physician specify two different tensions for standing and sitting, the microprocessor calculates a sitting or standing tension using the physician-prescribed tension as a variable.

Figure 5:
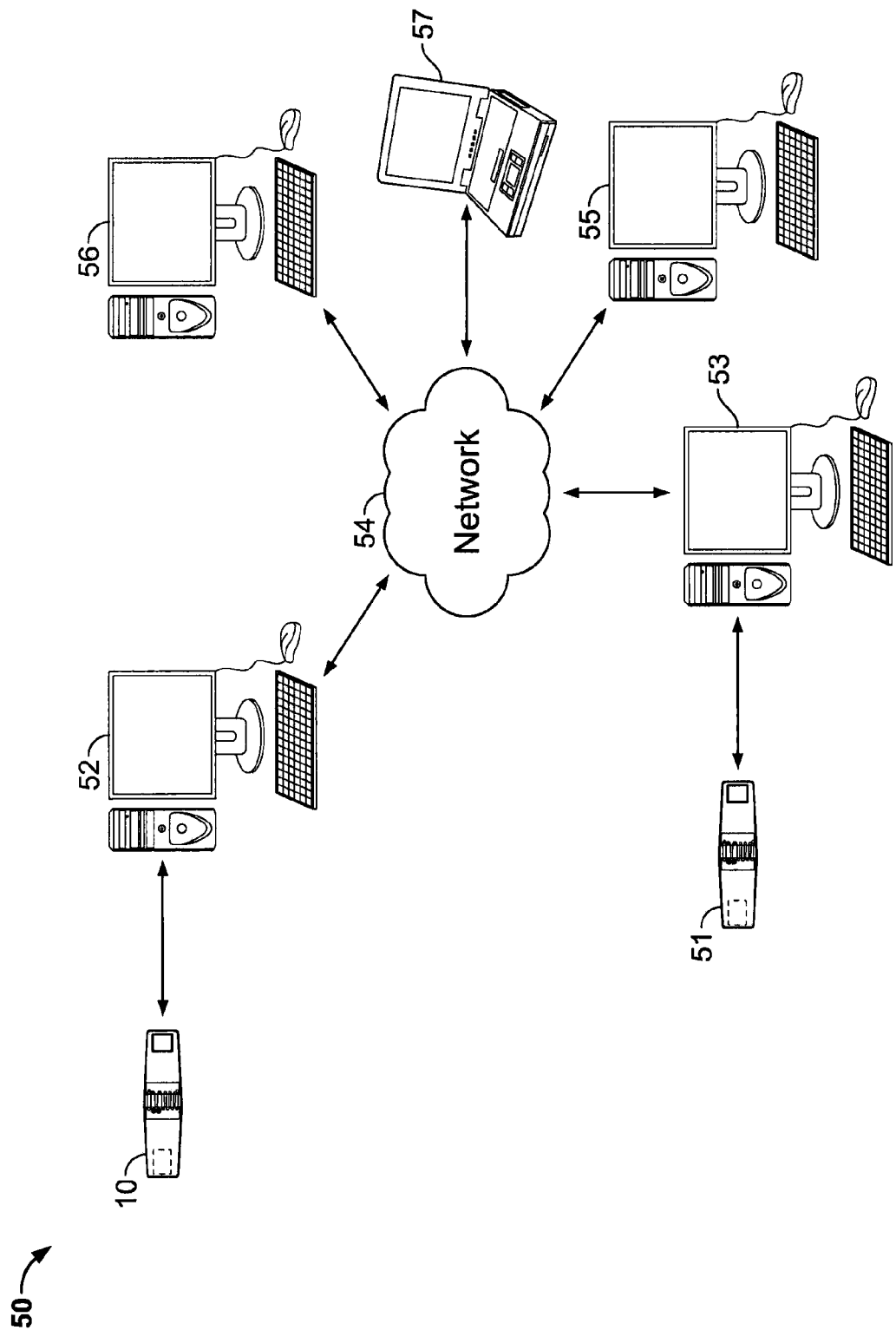
FIG. 5 is a block diagram of a network system, in accordance with an embodiment of the present invention.

With reference to FIG. 5, there is shown a block diagram of a network system 50, in accordance with an embodiment of the present invention. The system comprises the automated orthotic device 10, a patient's personal computer 52, a wide area network 54, and a physician's personal computer 56. The orthotic device 10 connects to the patient's personal computer 52 through an interface device 40. Examples of such an interface device include a USB connection, a WiFi connection, and a Bluetooth connection. In one embodiment, the user may want to share his or her information with other network users, such as an insurance provider or other physicians on the network. As such, there may be additional entities in the network system 50, such as additional automated orthotic devices 51, additional patient personal computers 53, additional physician's computers 55, and computers associated with insurance providers or other entities 57 that may have an interest in sending or receiving information over network system 50.

The patient's personal computer 52 includes hardware, software, and/or firmware generally operative to (1) receive recorded data from the orthotic device 10; (2) store the recorded data; (3) transmit data over the wide area network to a physician's personal computer 56; (4) receive data over the wide area network from a physician's personal computer 56; and (5) transmit data to the orthotic device 10. The patient's personal computer 52 may comprise a computer-readable storage medium, such as a hard disk drive, a human interface device ("HID") application programming interface ("API"), and a communication interface, such as a modem. The communication interface is coupled to the wide area network 54.

The wide area network 54 can be the Internet. Although FIG. 5 shows only one wide area network, it will be understood that multiple wide area networks may be used in the present invention. Also, although FIG. 5 only shows two patients' computers 52 and 53 and two physicians' computers 55 and 56, it will be understood that there may be more or fewer patients' computers and physicians' computers on the wide are network.

The physician's personal computer 56 includes hardware, software, and/or firmware generally operative to (1) receive data over the wide area network from a patient's personal computer 52; (2) store data; and (3) transmit data over the wide area network to a patient's personal computer 52 in order to program the orthotic device 10 with a certain tension prescription. The physician's personal computer may also be operative to receive data directly from and transmit data directly to the orthotic device 10 without the patient's computer, for example, if the patient were to make an in-office visit. The physician's personal computer 56 may comprise a computer-readable storage medium such as a hard disk drive, a human interface device ("HID") application programming interface ("API"), and a communication interface, such as a modem. The communication interface is coupled to the wide area network 54.

Figure 6:
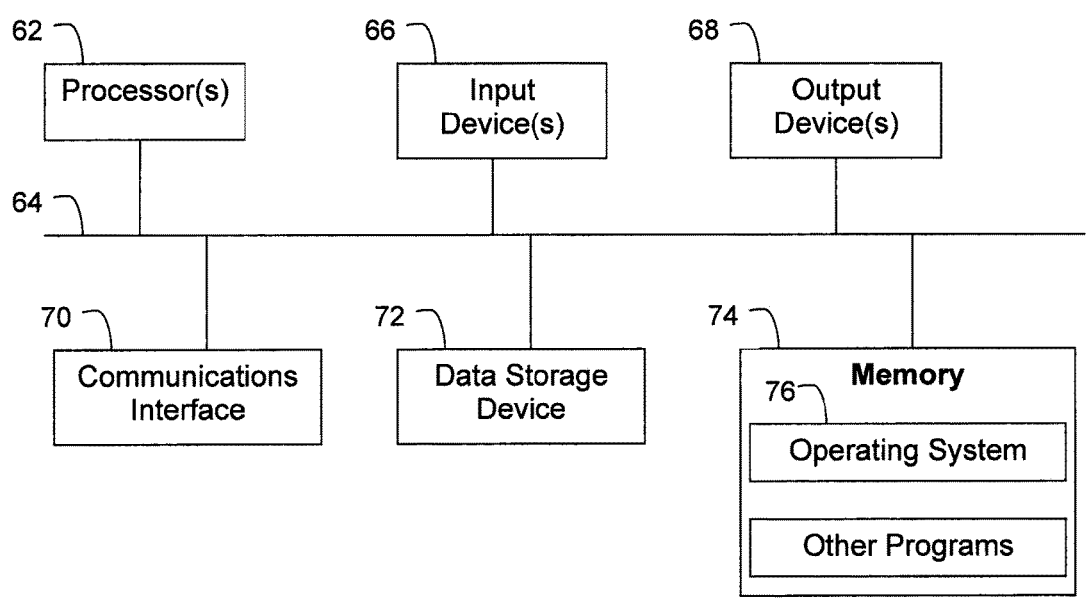
FIG. 6 is a block diagram of a computer system, in accordance with an embodiment of the present invention.

With reference to FIG. 6, there is shown a block diagram of a computer system. The computer system includes a processor 62, such as an Intel Pentium microprocessor or a Motorola Power PC microprocessor, coupled to a communications channel 64. The computer system further includes an input device 66 (such as a keyboard or mouse), an output device 68 (such as a liquid crystal display, a cathode ray tube display, or a plasma display), a communications interface 70, a data storage device 72 (such as a magnetic or optical disk), and memory 74 (such as random access memory (RAM)), each coupled to the communications channel 64. The communications interface 70 may be coupled to the wide area network 54. One skilled in the art will recognize that, although the data storage device 72 and memory 74 are shown as different units, the data storage device 72 and memory 74 may be parts of the same unit, distributed units, virtual memory, etc. Further, it will be appreciated that the term "memory" herein is intended to cover all data storage media, whether permanent or temporary.

The data storage device and/or the memory may also store an operating system (not shown), such as Microsoft Windows 7, Linux, the IBM OS/2 operating system, the MAC OS, or the UNIX operating system. It will be appreciated that embodiments of the present invention may also be implemented on platforms and operating systems other than those mentioned. An embodiment of the present invention may be written using JAVA, C, C++ language, or other programming languages, possibly using object oriented programming methodology.

One skilled in the art will recognize that the computer system of FIG. 6 may also include additional components, such as network connections, additional memory, additional processors, local area networks (LANs), and input/output lines for transferring information across a hardware channel, the Internet, or an intranet. One skilled in the art will also appreciate that the programs and data may be received by and stored in the computer system in alternative ways. For example, a computer-readable storage medium (CRSM) reader, such as a magnetic disk drive, hard disk drive, magneto-optical reader, or CPU, may be coupled to the communications channel 64 for reading a computer-readable storage medium (CRSM), such as a magnetic disk, a hard disk, a magneto-optical disk, or RAM.

Figure 7:
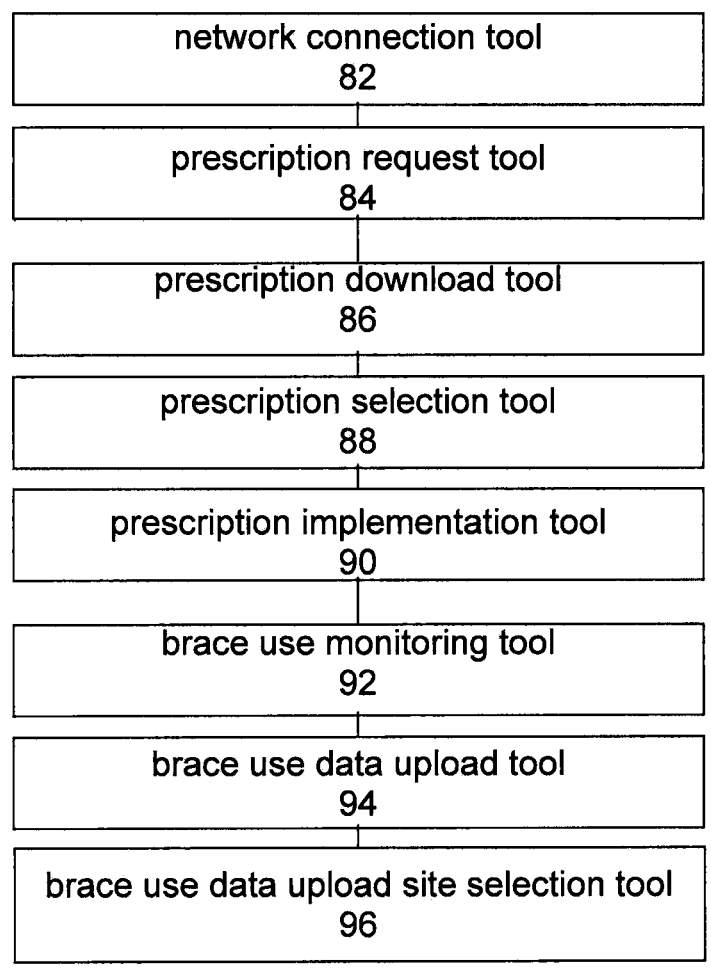
FIG. 7 is a block diagram of an automated orthotic device with treatment regimen system, in accordance with an embodiment of the present invention.

With reference to FIG. 7, there is shown a block diagram of an automated orthotic device with treatment regimen system 80 in accordance with an embodiment of the present invention. The automated orthotic device with treatment regimen system 80 may be implemented on the controller 34. The automated orthotic device with treatment regimen system 80 may include a network connection tool 82, a prescription request tool 84, a prescription download tool 86, a prescription selection tool 88, a prescription implementation tool 90, a brace use monitoring tool 92, a brace use data upload tool 94, and a brace use data upload site selection tool 96.

The network connection tool 82 includes hardware, software, and/or firmware generally operative to connect the controller 34 to a network or a computer. This connection allows the automated orthotic device controller to transfer brace use data to the network and receive prescription data from the network.

The prescription request tool 84 includes hardware, software, and/or firmware generally operative to request prescription data from a physician's computer, either directly or over a network.

The prescription download tool 86 includes hardware, software, and/or firmware generally operative to download and store prescription data, which may be in the form of a treatment regimen, from a physician's computer.

The prescription selection tool 88 includes hardware, software, and/or firmware generally operative to select a prescribed tension setting from a treatment regimen which includes one or more prescribed tension settings. This may occur manually, with the user selecting when he or she would like to switch from one setting to the other, or it may occur automatically, with the prescribed tension setting being changed automatically after a certain amount of time or after a certain number of hours that the back brace has been used.

The prescription implementation tool 90 includes hardware, software, and/or firmware generally operative to implement a prescribed tension setting. In one embodiment, the prescription implementation tool implements a prescribed tension setting by sending electrical signals to the motor 22.

The brace use monitoring tool 92 includes hardware, software, and/or firmware generally operative to monitor the patient's use of the brace and to store the brace use data. The brace use data may include such information as an hour-by-hour account of the patient's use of the back brace and the tension setting of the brace during use. In one embodiment, the brace use monitoring tool monitors the patient's use of the brace by periodically checking the current consumption of the motor 22, which is directly proportional to the brace tension, and comparing it with what it should be in accordance with the last set tension, as described above.

The brace use data upload tool 94 includes hardware, software, and/or firmware generally operative to upload the brace use data from the controller 34 to the network. Uploading this data to the network may include uploading the brace use data to the user's computer, or to the physician's computer, or to some other computer or device on the network.

The brace use data upload site selection tool 96 includes hardware, software, and/or firmware generally operative to allow the user to select where on the network they would like to upload the brace use data. In one embodiment, the brace use data upload site selection tool allows the user to select a location on the network by displaying a menu of network location for selection by the user.

In one embodiment, the automated orthotic device with treatment regimen system 80 allows the automated orthotic device 10 to interface with the network by uploading the user's back brace use data and also by downloading the user's treatment regimen prescription information. This system allows the automated orthotic device 10 to receive and implement an entire treatment regimen whereby the prescribed tension setting may be changed as the user's condition changes without the user being required to make multiple visits to the physician's office. This system also allows the user to receive changes to his or her prescribed treatment regimen over a network so that he or she does not have to go to the physician's office to receive these changes.

Figure 8:
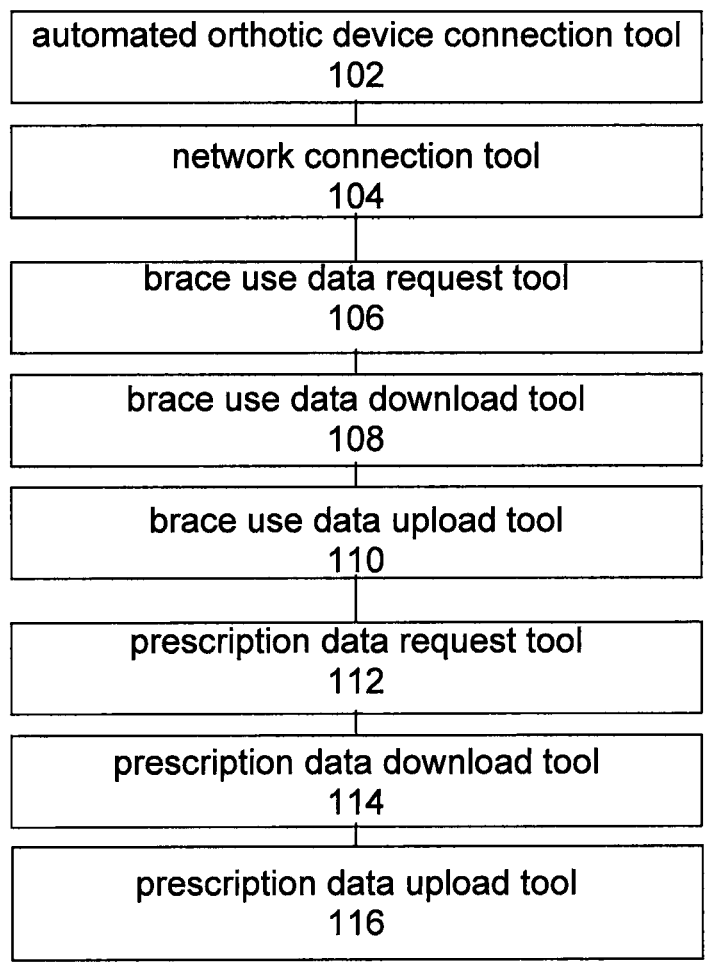
FIG. 8 is a block diagram of a user PC automated orthotic device interface system, in accordance with an embodiment of the present invention.

With reference to FIG. 8, there is shown a block diagram of a user PC automated orthotic device interface system 100, in accordance with an embodiment of the present invention. The user PC automated orthotic device interface system 100 may be implemented on a user's PC 52. The user PC automated orthotic device interface system 100 includes an automated orthotic device connection tool 102, network connection tool 104, a brace use data request tool 106, a brace use data download tool 108, a brace use data upload tool 110, a prescription data request tool 112, a prescription data download tool 114, and a prescription data upload tool 116.

The automated orthotic device connection tool 102 includes hardware, software, and/or firmware generally operative to connect the user's PC to automated orthotic device 10. This connection allows the user's PC to transfer prescription data to the automated orthotic device 10 and receive brace use data from the automated orthotic device 10.

The network connection tool 104 includes hardware, software, and/or firmware generally operative to connect the user's PC to a network. This connection allows the user's PC to transfer brace use data to the network and receive prescription data from the network.

The brace use data request tool 106 includes hardware, software, and/or firmware generally operative to request brace use data from the controller 34 on the automated orthotic device 10.

The brace use data download tool 108 includes hardware, software, and/or firmware generally operative to download and store brace use data from the controller 34 on the automated orthotic device 10.

The brace use data upload tool 110 includes hardware, software, and/or firmware generally operative to upload brace use data that has been downloaded from the controller 34, to the physician's PC 56.

The prescription data request tool 112 includes hardware, software, and/or firmware generally operative to request prescription data from the physician's PC 56.

The prescription data download tool 114 includes hardware, software, and/or firmware generally operative to download and store prescription data from the physician's PC 56.

The prescription data upload tool 116 includes hardware, software, and/or firmware generally operative to upload prescription that has been downloaded from the physician's PC 56, to the controller 34 on the automated orthotic device 10.

In one implementation, the user PC automated orthotic device interface system allows the user PC 52 to act as a connection tool between the automated orthotic device 10 and the physician's PC 56. The user PC 52 receives brace use data from the automated orthotic device 10 and uploads that information to the physician's PC 56. The user PC 52 also receives prescription data from the physician's PC 56 and sends it to the automated orthotic device 10.

Figure 9:
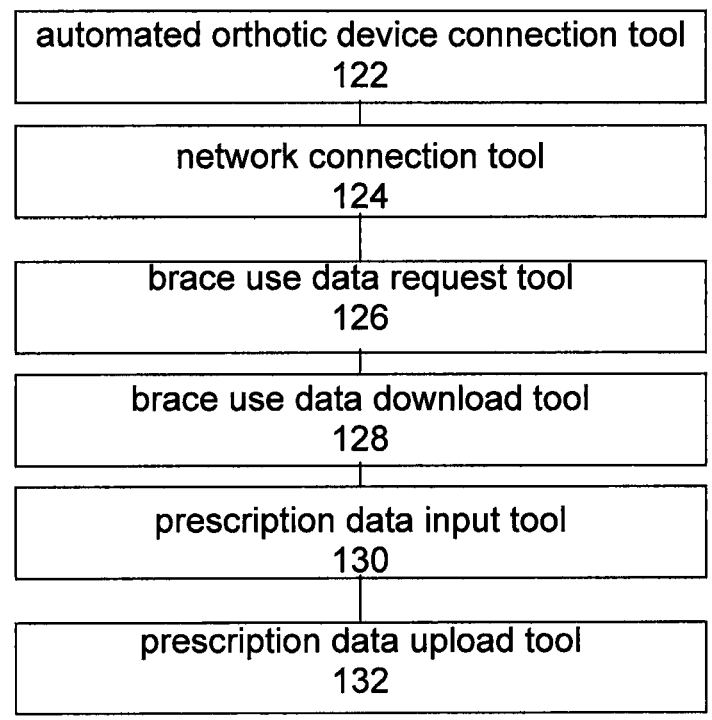
FIG. 9 is a block diagram of a physician's PC automated orthotic device interface system, in accordance with an embodiment of the present invention.

With reference to FIG. 9, there is shown a block diagram of a physician PC automated orthotic device interface system 120 in accordance with an embodiment of the present invention. In one embodiment, the user PC automated orthotic device interface system 120 may be implemented on a physician's PC 56. The physician PC automated orthotic device interface system 120 includes an automated orthotic device connection tool 122, network connection tool 124, a brace use data request tool 126, a brace use data download tool 128, a prescription data input tool, and a prescription data upload tool 132.

The automated orthotic device connection tool 122 includes hardware, software, and/or firmware generally operative to connect the physician's PC to the automated orthotic device 10. This connection allows the physician's PC to transfer prescription data to the automated orthotic device 10 and receive brace use data from the automated orthotic device 10. This connection would occur when the user visits the physician's office and the physician is able to directly connect his or her computer to the user's automated orthotic device 10.

The network connection tool 124 includes hardware, software, and/or firmware generally operative to connect the physician's PC to a network. This connection allows the physician's PC to receive brace use data from the network and transfer prescription data to the network.

The brace use data request tool 126 includes hardware, software, and/or firmware generally operative to request brace use data from the network (e.g., request brace use data stored on the user's PC) or directly from the controller 34 on the automated orthotic device 10.

The brace use data download tool 128 includes hardware, software, and/or firmware generally operative to download and store, on the physician's PC, brace use data from the network (e.g., brace use data that was saved on the user's PC) or from the controller 34 on the automated orthotic device 10.

The prescription input tool 130 includes hardware, software, and/or firmware generally operative to allow the physician to input a treatment regimen or prescription into the physician's computer for transferring to the automated orthotic device 10.

The prescription data upload tool 132 includes hardware, software, and/or firmware generally operative to upload prescription data to the network or directly to the controller 34 on the automated orthotic device 10.

In one embodiment, the physician PC automated orthotic device interface system 120 allows the physician PC 56 to receive brace use data and to transmit prescription data. The brace use data may be received through a direct connection between the automated orthotic device 10 and the physician's PC 56, possibly through a USB cable connecting the two, or the data may be received over a network connection between the automated orthotic device 10 and the physician's PC 56. Prescription data may be transmitted from the physician's PC 56 to the automated orthotic device 10 in the same ways, through a direct connection or through a network connection.

Figure 10:
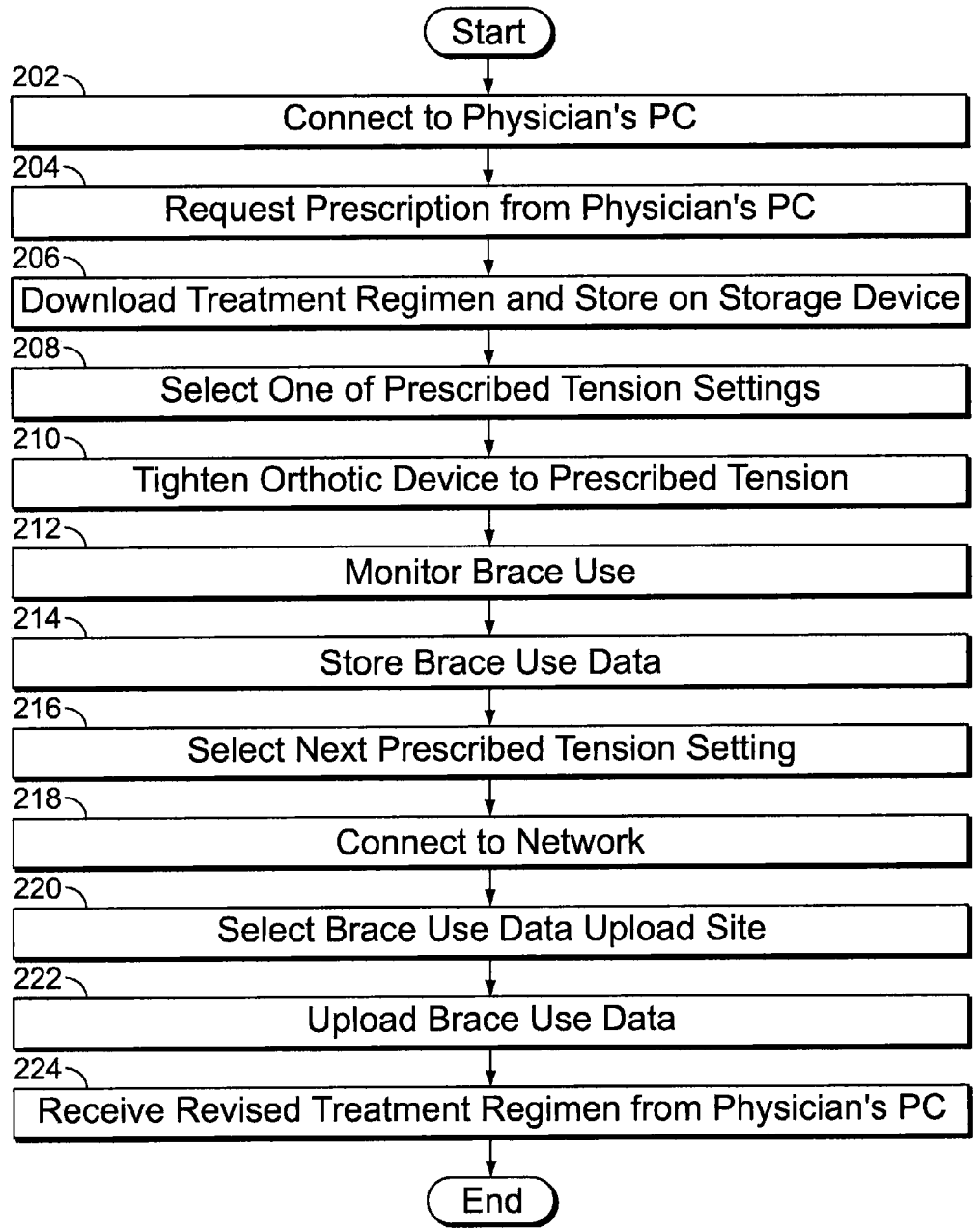
FIG. 10 is a flowchart of an automated orthotic device treatment regimen method, in accordance with an embodiment of the present invention.

With reference to FIG. 10, there is shown a flowchart of an automated orthotic device treatment regimen method 200, in accordance with an embodiment of the present invention. The method starts in step 202, where the automated orthotic device 10 connects to the physician's PC 56. This connection may be a direct connection, for example, by USB or bluetooth connection, or it may be a connection over a network, such as through a WiFi or ethernet connection. In step 204, the controller 34 on the automated orthotic device 10 requests a prescription from the physician's PC 56. This prescription may be a single prescribed tension setting for the automated orthotic device, or it may be a treatment regimen with multiple prescribed tension settings to apply varying levels of tension as the patient's condition changes or as time goes on. In one embodiment, the physician's PC provides a prescription without a request from the automated orthotic device 10. In step 206, the automated orthotic device 206 downloads the treatment regimen and stores it on the storage device 46.

If there are multiple prescribed tension settings, then a single one is chosen to be applied according to the specified order in the treatment regimen. This selection occurs in step 208, and may be a step taken by the user through the controller 34 or a step performed automatically by the controller 34. In one embodiment, the controller 34 allows for the user to manually select which prescribed tension setting will be applied when. In another embodiment, the treatment regimen may automatically switch from a first prescribed tension setting to a second prescribed tension setting after the passage of a specified amount of time. In yet another embodiment, the prescribed tension setting may change after a certain number of hours of use of the orthotic device by the user, which, as was explained earlier, the controller 34 is able to keep track of when the back brace is being used through continuous or periodic sensing.

Once a prescribed tension setting is chosen, the controller tightens the orthotic device to the prescribed tension setting in step 210. In step 212, through continuous or periodic sensing, the brace is able to monitor when the brace is being used and at what tension, and in step 214, stores the brace use data. If there are multiple prescription settings in the treatment regimen, step 216 changes the prescribed tension setting in order to better suit the user's changing condition. As was described earlier, this change may be initiated by the user as he or she feels that his or her treatment is progressing, or it may occur automatically after the passage of a certain amount of time.

When the user wishes to communicate with his or her doctor without going into the physician's office, the user may move to step 218 and connect the automated orthotic device 10 to the network 50. In one embodiment, the user may also want to share his or her information with other network users, such as an insurance provider or other physicians on the network. At step 220, the user may specify where they want to upload the brace use data that is stored on controller 34 in the storage device 46. At step 222, brace use data is uploaded to the specified site.

If the user is connected to a physician's computer, the user or the physician may want to alter the treatment regimen. At step 224, the physician may transfer to the user's automated orthotic device 10 a revised treatment regimen, which would return the method to step 208 to choose a prescribed tension setting from the treatment regimen.

Figure 11:
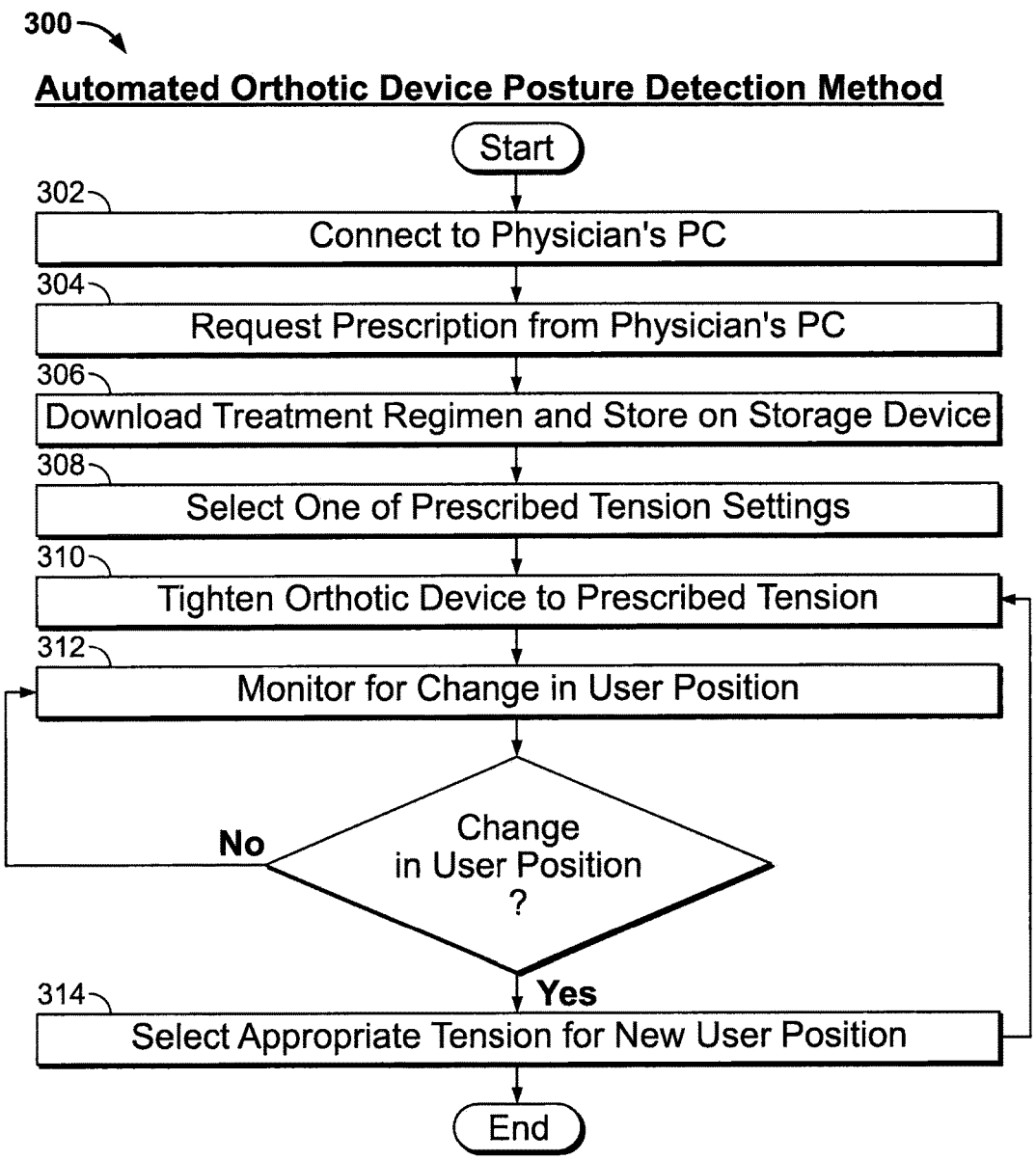
FIG. 11 is a flowchart of an automated orthotic device posture detection method 300, in accordance with an embodiment of the present invention.

With reference to FIG. 11, there is shown a flowchart of an automated orthotic device posture detection method 300, in accordance with an embodiment of the present invention. The method starts in step 302, where the automated orthotic device 10 connects to the physician's PC 56. This connection may be a direct connection, for example, by USB or bluetooth connection, or it may be a connection over a network, such as through a WiFi or ethernet connection. In step 304, the controller 34 on the automated orthotic device 10 requests a prescription from the physician's PC 56. This prescription may be a single prescribed tension setting for the automated orthotic device, or it may be a treatment regimen with multiple prescribed tension settings to apply varying levels of tension as the patient's condition changes or as time goes on. In one embodiment, the physician's PC provides a prescription without a request from the automated orthotic device 10. In step 206, the automated orthotic device 206 downloads the treatment regimen and stores it on the storage device 46.

If there are multiple prescribed tension settings, then a single one is chosen to be applied according to the specified order in the treatment regimen. This selection occurs in step 308, and may be a step taken by the user through the controller 34 or a step performed automatically by the controller 34. In one embodiment, the controller 34 allows for the user to manually select which prescribed tension setting will be applied when. In another embodiment, the treatment regimen may automatically switch from a first prescribed tension setting to a second prescribed tension setting after the passage of a specified amount of time. In yet another embodiment, the prescribed tension setting may change after a certain number of hours of use of the orthotic device by the user, which, as was explained earlier, the controller 34 is able to keep track of when the back brace is being used through continuous or periodic sensing.

Once a prescribed tension setting is chosen, the controller tightens the orthotic device to the prescribed tension setting in step 310. In one embodiment, each prescribed tension setting includes both a standing prescribed tension setting and a sitting prescribed tension setting, with each of these settings individually specified by the physician. In another embodiment, rather than having the patient's physician specify two different tensions for standing and sitting, the microprocessor calculates a sitting or standing tension using the physician-prescribed tension as a variable. In step 312, the posture detection device 42 monitors for any change in user posture or position. In one embodiment, the posture detection device 42 is an accelerometer. If no change in posture is detected, the automated orthotic device 10 continues to apply the current prescribed tension setting (e.g., the standing prescribed tension setting). When a change in posture occurs, the microprocessor 38 analyzes data from the posture detection device 42 to determine whether the user is now standing or sitting. Once the user's position is determined, the orthotic device 10 determines the appropriate prescribed tension setting at step 314, whether it is for standing or for sitting. Once the appropriate tension setting is determined, the method returns to step 310, where the tension setting is applied.

Although the invention has been disclosed with reference only to the presently preferred embodiments, those of ordinary skill in the art will appreciate that various modifications can be made without departing from the invention. Accordingly, the invention is defined only by the following claims.

What is claimed is:

1. An automated orthotic device with a treatment regimen program, the device comprising:
 a body brace configured to be worn around the trunk of a patient;
 a data storage device;
 a controller;
 a patient position detection device or a posture detection device configured to automatically determine whether the patient is standing or sitting;
 wherein the data storage device stores a treatment regimen program that has been determined by a physician, the treatment regimen being a single prescribed tension setting or comprising a plurality of prescribed tension settings to be carried out in a specified order;
 wherein the patient position detection device is configured to automatically adjust the tension setting in response to a change in a position of the patient;
 wherein the controller is configured to carry out the treatment regimen program by causing the body brace to apply each of the plurality of prescribed tension settings according to the specified order of the treatment regimen program or to automatically set the orthotic device to different tension settings when the patient is sitting and when the patient is standing.

2. The automated orthotic device of claim 1, wherein the treatment regimen program further comprises a plurality of set periods of time, each of set periods of time of the plurality of set periods of time being associated with at least one of the plurality of prescribed tension settings, and wherein the controller is further configured to carry out the treatment regimen program by:
 causing the body brace to apply a first prescribed tension setting for the set period of time associated with the first prescribed tension setting, and then
 automatically applying a next prescribed tension setting for the set period of time associated with the next prescribed tension setting until the treatment regimen program is completed and each of the plurality of prescribed tension settings has been applied according to the specified order of the treatment regimen program.

3. The automated orthotic device of claim 1, wherein the controller is configured to apply a first one of the plurality of prescribed tension settings until a user inputs a command to switch to a next prescribed tension setting until the treatment regimen program is completed and each of the plurality of prescribed tension settings has been applied according to the specified order of the treatment regimen program.

4. The automated orthotic device of claim 1, wherein the body brace and controller are further configured to detect and store brace usage data on the data storage device, wherein the brace usage data includes data on the length of time the patient has worn the automated orthotic device and data on the tension settings applied while being worn.

5. The automated orthotic device of claim 4, wherein the treatment regimen program further comprises a plurality of set periods of time, each of the plurality of set periods of time being associated with at least one of the plurality of prescribed tension settings, wherein each set period of time specifies a period of time that the automated orthotic device must be worn by the patient at a prescribed tension setting, and wherein the controller is further configured to carry out the treatment regimen program by:
  causing the body brace to apply a first prescribed tension setting until the patient has worn the automated orthotic device at the first prescribed tension setting for the time period specified in the treatment regimen program, and then
  automatically applying the next prescribed tension setting until the patient has worn the automated orthotic device at the next prescribed tension setting for the period of time specified in the treatment regimen program, and
  automatically advancing to the next prescribed tension setting until the treatment regimen program is completed and each of the plurality of prescribed tension settings has been applied according to the specified order of the treatment regimen program.

6. The automated orthotic device of claim 1, further comprising a network connection device, wherein the network connection device allows the controller to receive data from a network and transmit data to the network.

7. The automated orthotic device of claim 6, wherein the controller is configured to receive a treatment regimen program from a remote computer through the network connection device.

8. The automated orthotic device of claim 1, wherein the controller is configured to automatically cause the body brace to apply a first position-dependent tension setting when the patient is in a first position, and a second tension position-dependent setting when the patient is in a second position.

9. The automated orthotic device of claim 1, wherein the patient position detection device is an accelerometer.

10. An automated orthotic device with a treatment regimen program, the device comprising:
  a body brace comprising two brace segments and an automatic brace tensioning device, the two brace segments being configured to be fitted around the trunk of a patient, the automatic brace tensioning device adjustably connecting the two brace segments to each other;
  a data storage device configured to store a treatment regimen program;
  a measuring device configured to automatically detect whether the patient is sitting or standing;
  a controller configured to control the automatic brace tensioning device under the treatment regimen program to automatically move the two brace segments toward and away from each other in a manner varying tension in the body brace, the controller configured to automatically adjust the body brace to a first adjusted position upon the measuring device detecting that the patient is standing, the controller configured to automatically adjust the body brace to a second adjusted position upon the measuring device detecting that the patient is sitting.

11. The automated orthotic device of claim 10, wherein the two brace segments are moved by tightening or loosening a cable extending between the two brace segments.

12. The automated orthotic device of claim 10, wherein the automatic brace tensioning device is motorized.

13. The automated orthotic device of claim 10, wherein the two brace segments each have a first end and a second end, the first ends being removably securable to each other and the second ends being connected by the automatic brace tensioning device.

14. The automated orthotic device of claim 10, wherein the controller is configured to automatically cause the body brace to apply a first position-dependent tension setting when the patient is in a first position, and a second tension position-dependent setting when the patient is in a second position.

15. An automated orthotic device with a treatment regimen program, the device comprising:
  a body brace, comprising:
    a plurality of brace segments;
    a plurality of pulleys positioned on the brace segments;
    a cable positioned around the plurality of pulleys, the cable having an operative length;
    a motor configured to adjust the operative length of the cable;
  a patient position detection device or a patient posture detection device configured to automatically determine whether a patient wearing the body brace is standing or sitting;
  a data storage device configured to store a treatment regimen program;
  a controller configured to control the motor using the treatment regimen program to automatically adjust the operative length of the cable, the controller configured to automatically adjust the body brace based at least in part on the determined standing or sitting position of the patient.

16. The automated orthotic device of claim 15, wherein the motor adjusts the operative length of the cable by reeling or unreeling the cable.

17. The automated orthotic device of claim 15, wherein the cable is reeled around a motor shaft.

18. The automated orthotic device of claim 15, wherein the motor adjusts the operative length of the cable by turning a plurality of gears.

19. The automated orthotic device of claim 18, wherein the plurality of gears comprises at least one worm gear and at least one worm.

20. The automated orthotic device of claim 19, wherein the cable is wound around at least one spool coupled to the at least one worm gear.

21. The automated orthotic device of claim 15, further comprising a plurality of plates attached to the plurality of brace segments, the plurality of pulleys being mounted to the plurality of plates.

* * * * *